United States Patent
Ragauskas (10) Patent No.: US 7,147,605 B2
(45) Date of Patent: Dec. 12, 2006

(54) METHOD AND APPARATUS FOR NONINVASIVE DETERMINATION OF THE ABSOLUTE VALUE OF INTRACRANIAL PRESSURE

(75) Inventor: Arminas Ragauskas, Kaunas (LT)

(73) Assignee: UAB Vittamed (LT)

( * ) Notice: Subject to any disclaimer, the term of this patent is extended or adjusted under 35 U.S.C. 154(b) by 459 days.

(21) Appl. No.: 10/615,186

(22) Filed: Jul. 8, 2003

(65) Prior Publication Data

US 2004/0087871 A1    May 6, 2004

Related U.S. Application Data

(60) Provisional application No. 60/394,410, filed on Jul. 8, 2002.

(51) Int. Cl.
*A61B 5/00* (2006.01)
*A61B 5/103* (2006.01)

(52) U.S. Cl. ......................... 600/561; 600/587
(58) Field of Classification Search ................ 600/561, 600/587
See application file for complete search history.

(56) References Cited

U.S. PATENT DOCUMENTS

| | | | |
|---|---|---|---|
| 3,610,233 A * | 10/1971 | Barkalow | 601/106 |
| 4,246,908 A * | 1/1981 | Inagaki et al. | 600/561 |
| 4,505,278 A * | 3/1985 | Alban | 600/587 |
| 4,564,022 A | 1/1986 | Rosenfeld et al. | |
| 4,841,986 A * | 6/1989 | Marchbanks | 600/559 |
| 4,971,061 A | 11/1990 | Kageyama et al. | |
| 4,984,567 A | 1/1991 | Kageyama et al. | |
| 4,995,401 A | 2/1991 | Bunegin et al. | |
| 5,074,310 A | 12/1991 | Mick | |
| 5,117,835 A | 6/1992 | Mick | |
| 5,291,899 A * | 3/1994 | Watanabe et al. | 600/561 |
| 5,388,583 A | 2/1995 | Ragauskas et al. | |
| 5,411,028 A | 5/1995 | Bonnefous | |
| 5,617,873 A | 4/1997 | Yost et al. | |
| 5,919,144 A | 7/1999 | Bridger et al. | |
| 5,951,477 A | 9/1999 | Ragauskas et al. | |
| 5,993,398 A | 11/1999 | Alperin | |

(Continued)

FOREIGN PATENT DOCUMENTS

WO    WO 01/54584 A1    1/2000

(Continued)

OTHER PUBLICATIONS

Buki B., Chomicki A., Dordain M., Lemaire J.J., Wit H.P., Chazal J., Avan P.; Middle ear influence on otoacoustic emissions. II: contributions of posture and intracranial pressure; National Library of Medicine.

(Continued)

*Primary Examiner*—Max F. Hindenburg
*Assistant Examiner*—Michael Apanius
(74) *Attorney, Agent, or Firm*—St. Onge Steward Johnston & Reens LLC (57) ABSTRACT

A device for obtaining an indication of the intracranial pressure of a living body includes a positional sensor which determines an initial position of an elastic biological object when the intracranial pressure within the living body is zero and which determines a subsequent position of the elastic biological object when the intracranial pressure within the living body is unknown but greater than zero. A pressure generator applies an external pressure to the elastic biological object, and a comparator compares the initial position with the subsequent position so as to identify the unknown intracranial pressure of the living body as that external pressure which causes the subsequent position to be equal to the initial position.

12 Claims, 7 Drawing Sheets

U.S. PATENT DOCUMENTS

| | | |
|---|---|---|
| 6,117,089 A | 9/2000 | Sinha |
| 6,129,682 A | 10/2000 | Borchert et al. |
| 6,231,509 B1 | 5/2001 | Johnson et al. |
| 6,245,027 B1 | 6/2001 | Alperin |
| 6,328,694 B1 | 12/2001 | Michaeli |
| 6,740,048 B1 * | 5/2004 | Yost et al. .................. 600/561 |
| 2001/0027335 A1 | 10/2001 | Meyerson et al. |
| 2001/0039386 A1 | 11/2001 | Johnson |

FOREIGN PATENT DOCUMENTS

| | | |
|---|---|---|
| WO | WO 00/68647 | 5/2000 |
| WO | WO 01/50944 A2 | 1/2001 |

OTHER PUBLICATIONS

Buki B., Avan P., Lemaire J.J., Dordain M., Chazal J. Ribari O.; Otoacoustic emissions: a new tool for monitoring intracranial pressure changes through stapes displacements; National Library of Medicine.

* cited by examiner

METHOD AND APPARATUS FOR NONINVASIVE DETERMINATION OF THE ABSOLUTE VALUE OF INTRACRANIAL PRESSURE

RELATED APPLICATIONS

This patent application claims the benefit of, under Title 35, United States Code, Section 119(e), U.S. Provisional Patent Application No. 60/394,410, filed Jul. 8, 2002.

FIELD OF THE INVENTION

The present invention relates to the noninvasive measurement and monitoring of the absolute value of intracranial pressure.

BACKGROUND OF THE INVENTION

The measurement of the absolute value of intracranial pressure (ICP) is important in diagnosing and treating various pathophysiological conditions caused by head trauma, hemorrhage tumors, inflammatory diseases and the like. Several techniques have been used to measure ICP. Conventional invasive ICP measurement techniques require surgical passage through the skull bone into the brain ventricles, parenchyma or the region between the skull and dura matter to implant a measuring transducer. Such invasive techniques, however, are undesirable, as damage to the sensitive brain tissues may result. Moreover, due to the invasive nature of the procedures, infections may be caused despite precautions, which infections can be serious or even deadly.

Various systems and methods for the noninvasive measurement of ICP have been suggested. Several of these techniques rely upon ultrasonic imaging to detect relative displacements of tissue boundaries within the brain. The displacements may be associated with fluid build-up and compression or dilation of brain vessels, which permits determination of ICP through an independent calibration of compressibility. An alternate noninvasive ultrasonic technique involves the measurement of blood flow in the carotid artery by ultrasonic excitation of the artery and determination of Doppler frequency shift. Examples of various types of ultrasonic measurement techniques are disclosed in U.S. Pat. No. 5,074,310 to Mick and U.S. Pat. No. 5,117,835 again to Mick, U.S. Pat. No. 5,388,583 to Ragauskas et al., U.S. Pat. No. 5,411,028 to Bonnefous, U.S. Pat. No. 5,617,873 to Yost et al., and U.S. Pat. No. 5,919,144 to Bridger et al. Each of the patents cited above is incorporated herein by reference.

Other noninvasive ICP measurement techniques that have been proposed involve determining the displacement of various tissues or body members. For example, it has been proposed, that ICP can be measured by observing the tympanic membrane of the ear. (See Buki B. et al., Otoacoustic Emissions: A New Tool For Monitoring Intracranial Pressure Changes Through Stapes Displacements, Hear Res 1996 May; 94 (1–2): 125–39; Buki B. et al., Middle Ear Influence On Otoacoustic Emissions—II: Contribution Of Posture And intracranial Pressure, Hear Res. 2000 February; 140 (1 –2):202–11; Reid A., Marchbanks R. J. et al., The Relationship Between Intracranial Pressure And Tympanic Membrane Displacement, British Journal of Audiology, 1990: 24:123–129; U.S. patent Publication No. 2001/0027335 A1). It has also been proposed that ICP in infants can be measured by observing the fontanelle. (See U.S. Pat. No. 4,995,401).

However, all of these proposed systems and methods suffer from at least one significant disadvantage. More specifically, while such systems and methods can be used to measure changes in ICP, such systems and methods can not be used to determine the absolute value of ICP without performing some type of calibration (for example, using known invasive techniques). This is true because displacement of various internal and external tissues or body members in response to various degrees of ICP is not the same from person to person. For example, the degree of distension of the tympanic membrane of the ear in one patient having a certain ICP may be completely different than in another patient having the exact same ICP due to numerous factors such as age, size, thickness of the tympanic membrane, degree of dehydration, etc. Thus, without performing some type of calibration for each patient, the absolute value of ICP for that patient can not be determined using the above methods. The dilemma is that if an individual noninvasive ICP absolute value measuring device exists with acceptable accuracy for calibration of other noninvasive ICP meters, the other meters are unnecessary.

A noninvasive ICP absolute value measuring method and apparatus is presented in U.S. Pat. No. 5,951,477 to Ragauskas et al., which is commonly owned with the present application, the entirety of which is incorporated by reference herein. This patent discloses the use of an ultrasonic Doppler device which detects the velocities of the blood flow inside the optic artery for both intracranial and extracranium optic artery portions, which velocities are used to calculate an absolute ICP. However, it would be more desirable if a simpler technique could be developed.

What is desired, therefore, is a system and method for determining the absolute value of ICP which is non-invasive, which can be used without performing calibration thereof, which is relatively simple to use, and which is safe and dependable.

SUMMARY OF THE INVENTION

Accordingly, it is an object of the present invention to provide a system and method for determining the absolute value of ICP which is non-invasive.

Another object of the present invention is to provide a system and method for determining the absolute value of ICP having the above characteristics and which can be used without performing calibration thereof.

A further object of the present invention is to provide a system and method for determining the absolute value of ICP having the above characteristics and which is relatively simple to use.

Still another object of the present invention is to provide a system and method for determining the absolute value of ICP having the above characteristics and which is safe and dependable.

These and other objects of the present invention are achieved in one embodiment by provision of a device for obtaining an indication of the intracranial pressure of a living body. The device includes a positional sensor which determines an initial position of an elastic biological object when the intracranial pressure within the living body is zero and which determines a subsequent position of the elastic biological object when the intracranial pressure within the living body is unknown but greater than zero. A pressure generator applies an external pressure to the elastic biological object, and a comparator compares the initial position with the subsequent position so as to identify the unknown intracranial pressure of the living body as that external pressure which causes the subsequent position to be equal to the initial position.

In some embodiments, the elastic biological object comprises a skull bone. In certain of these embodiments, the pressure generator comprises an inflatable helmet, while in others the pressure generator comprises a piston and cylinder assembly mounted on a frame. In some embodiments, the elastic biological object comprises a tympanic membrane of an ear. In certain of these embodiments, the pressure generator comprises a tube adapted for insertion into an ear.

In another embodiment, a device is provided for obtaining a measurement of the absolute pressure inside a cranium. The device includes a sensor for detecting positional changes of a physiological object whose position changes in response to changes in intracranial pressure. The device also includes a pressure generating device with which a pressure is applied to the physiological object to restore the physiological object to an initial position representative of an initial intracranial pressure. A pressure indicator senses the pressure applied by the pressure generating device and indicates the pressure.

In some embodiments, the physiological object comprises a skull bone. In certain of these embodiments, the pressure generating device comprises an inflatable helmet, while in others the pressure generating device comprises a piston and cylinder assembly mounted on a frame. In some embodiments, the physiological object comprises a tympanic membrane of an ear. In certain of these embodiments, the pressure generating device comprises a tube adapted for insertion into an ear.

In another aspect of the present invention, a method for obtaining an indication of the intracranial pressure of a living body is provided. In one embodiment of this method, an initial position of an elastic biological object is determined when the intracranial pressure within the living body is zero. A subsequent position of the elastic biological object when the intracranial pressure within the living body is unknown but greater than zero is also determined. An external pressure is applied to the elastic biological object, and the unknown intracranial pressure of the living body is identified as that external pressure which causes the subsequent position to be equal to the initial position.

In some embodiments, the elastic biological object comprises a skull bone. In certain of these embodiments, the applying an external pressure step comprises the step of inflating an inflatable helmet, while in others the applying an external pressure step comprises the step of actuating a piston and cylinder assembly mounted on a frame. In some embodiments, the elastic biological object comprises a tympanic membrane of an ear. In certain of these embodiments, the applying an external pressure step comprises the step of flowing fluid through a tube adapted for insertion into an ear.

In another embodiment of the inventive method of the present invention, a first position of a physiological object affected by intracranial pressure is determined when the intracranial pressure is balanced with atmospheric pressure. A force is applied against the physiological object until the position of the object is restored to its first position and storing a value of the force at which this occurs.

In some embodiments, the physiological object comprises a skull bone. In certain of these embodiments, the applying a force step comprises the step of inflating an inflatable helmet, while in others the applying a force step comprises the step of actuating a piston and cylinder assembly mounted on a frame. In some embodiments, the physiological object comprises a tympanic membrane of an ear. In certain of these embodiments, the applying a force step comprises the step of flowing fluid through a tube adapted for insertion into an ear.

The invention and its particular features and advantages will become more apparent from the following detailed description considered with reference to the accompanying drawings.

BRIEF DESCRIPTION OF THE DRAWINGS

FIG. 2b is a schematic view illustrating operation of the system of FIG. 2a;

FIG. 2c is a partially cross-sectional view illustrating in more detail a portion of the system of FIG. 2a;

DETAILED DESCRIPTION OF AN EMBODIMENT OF THE INVENTION

Figure 1A:
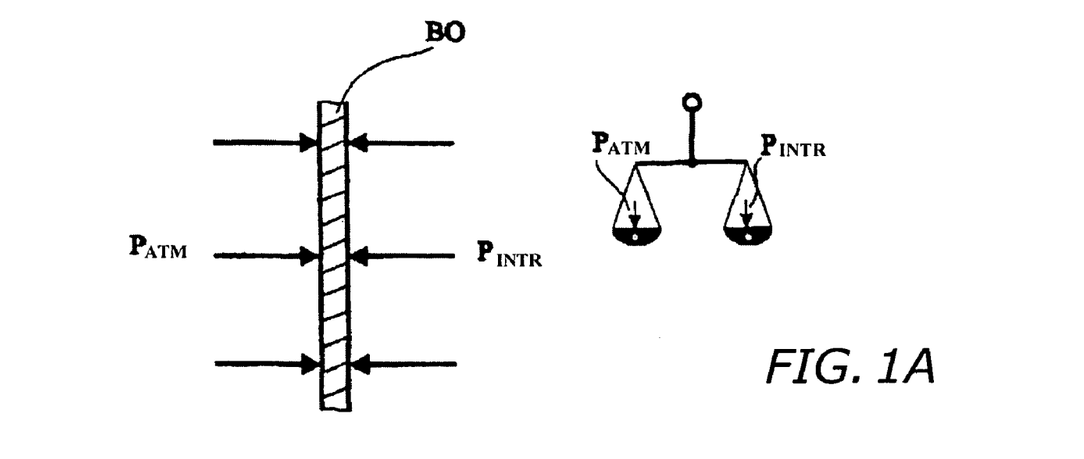
FIGS. 1a–1c are schematic views illustrating a scientific principle underlying the present invention.
Figure 1B:
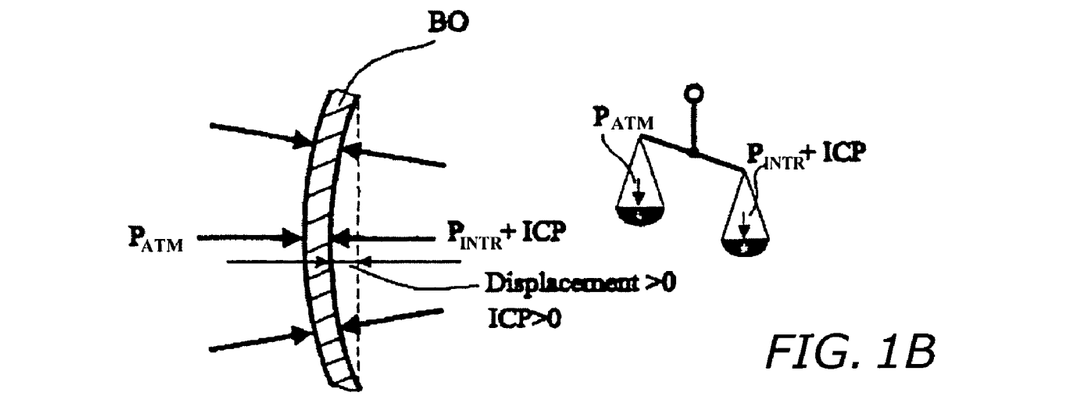
Figure 1C:
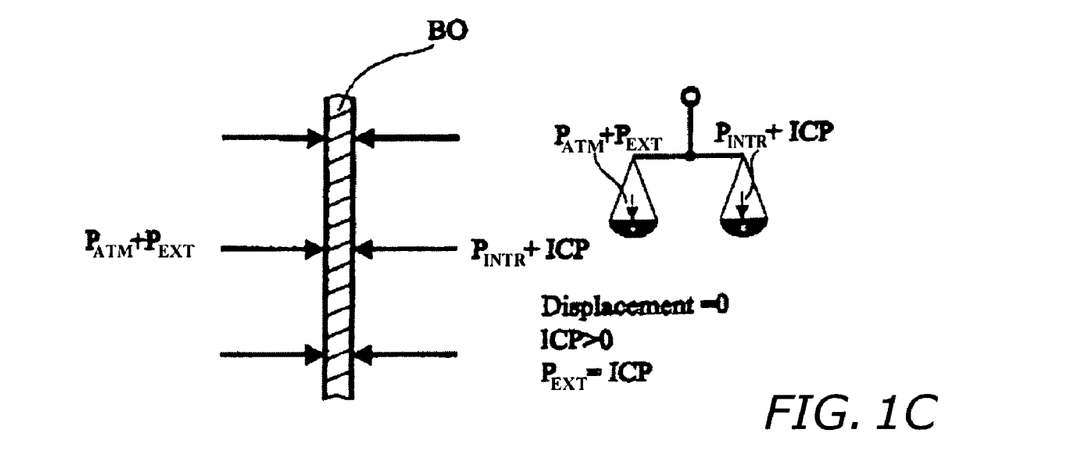

Referring first to FIGS. 1a–1c a scientific principle underlying the present invention is shown. FIG. 1a shows the typical situation where there is no intracranial pressure (ICP=0). Internal pressure $P_{INTR}$ is equal to the atmospheric pressure $P_{ATM}$, and the elastic biological object BO (e.g., the skull bone or tympanic membrane) has not been displaced from its initial position.

FIG. 1b shows where there is a positive intracranial pressure (ICP>0). The external forces on biological object BO (i.e., atmospheric pressure $P_{ATM}$) are no longer balanced with the internal forces on biological object BO (i.e., internal pressure $P_{INTR}$+intracranial pressure ICP), and elastic biological object BO is displaced outwardly.

FIG. 1c shows that by applying an external pressure $P_{EXT}$ to the biological object BO equal to the intracranial pressure ICP the biological object BO is displaced back to its initial position. When in this position, the external forces on biological object BO (i.e., atmospheric pressure $P_{ATM}$+ external pressure $P_{EXT}$) are now balanced with the internal forces on biological object BO (i.e., internal pressure $P_{INTR}$+ intracranial pressure ICP). Thus, it is known that:

$$P_{ATM}+P_{EXT}=P_{INTR}+ICP.$$

It is also known from above that atmospheric pressure $P_{ATM}$ equals internal pressure $P_{INTR}$ ($P_{ATM}=P_{INTR}$). As such, it must also be true that external pressure $P_{EXT}$ equals intracranial pressure ICP ($P_{EXT}=ICP$). Thus, by applying an increasing external pressure $P_{EXT}$, it is possible to determine intracranial pressure ICP by determining when the biological object BO is displaced back to its initial position (Displacement=0).

With a method in accordance with the invention the absolute pressure inside the cranium can be obtained by applying an external pressure to the cranium up to a level that will return the structure to its original position. The level of the external pressure that achieves this is deemed to be equal to the absolute intra-cranium pressure.

ICP generates within the patient's skull a stress in the form of internal pressure directed to the skull bones, intracranial arteries, veins and microvessels, cerebroventricles, tympanic membrane (through the cochlear aqueduct) and mechanical load on the stapes footplace. As the ICP varies so does the stress in the skull bone, tympanic membrane and other biological objects. It has been found that the skull bone and the tympanic membrane, among other biological objects, behave as curved elastic plates, thus making the scientific principle illustrated in FIGS. 1a–1c applicable.

The displaced elastic biological object (e.g., skull bones or tympanic membrane) can be moved to the initial location by an external pressure $P_{EXT}$ which is then equal to the intracranial pressure's ICP absolute value, as discussed above. The initial location of the biological object is determined under only one condition, namely, when ICP=0. It is not necessary to apply some individual calibration procedure in this case and the peculiarities of individual patients have no influence on the accuracy of the proposed absolute ICP measuring method of this invention.

Any existing measuring device or 3D imaging system sufficiently sensitive to respond to appropriate anatomical configuration changes of skull bones or tympanic membrane caused by ICP changes can accordingly be used for absolute balance, when $P_{EXT}$=ICP, determinations applying the method disclosed herein. When the external pressure $P_{EXT}$ attains a value at which the displaced biological object is moved to its initial location, then the external pressure needed to achieve that condition is deemed to be equal to the absolute value of the intra-cranial pressure.

Figure 2A:
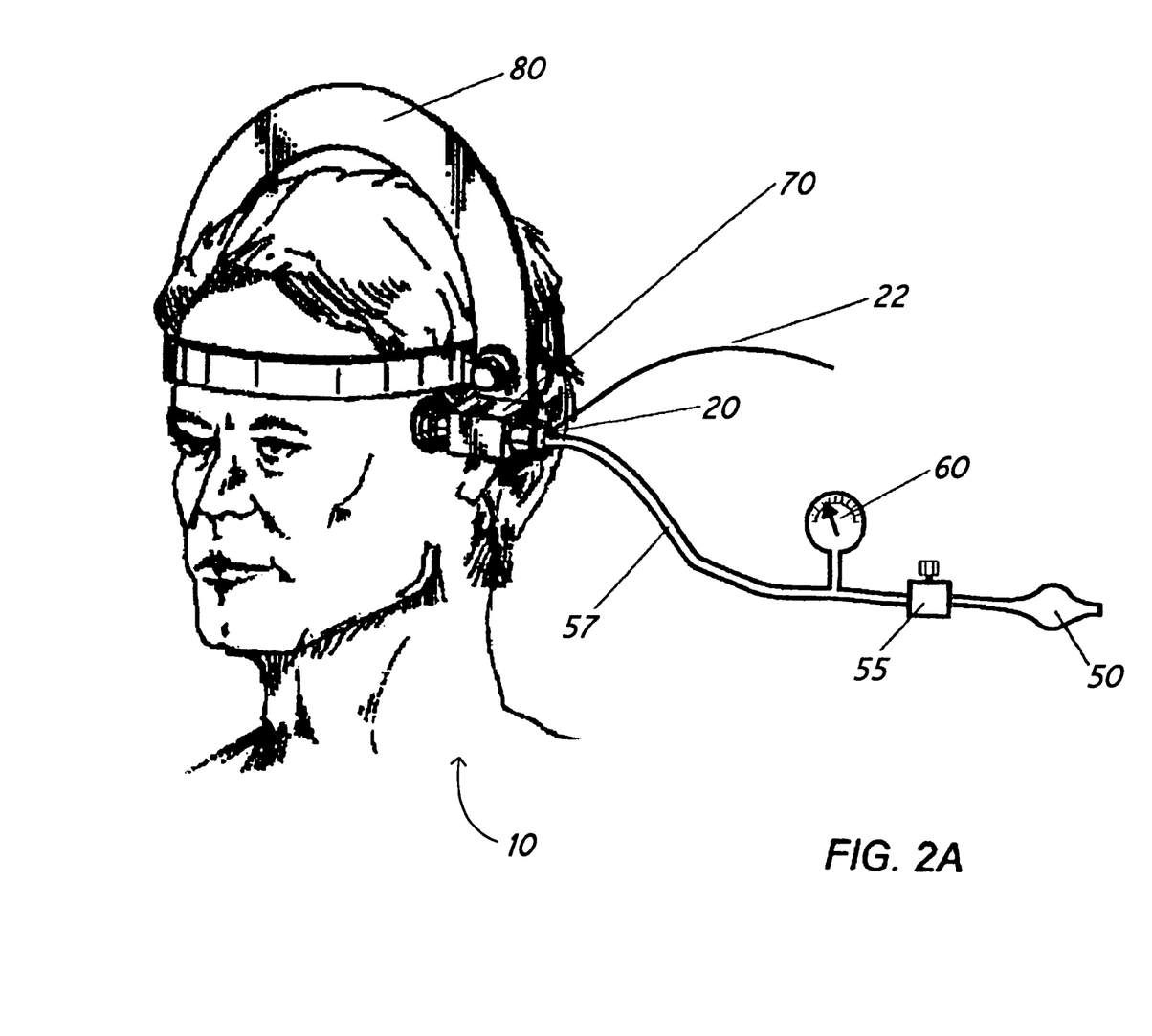
FIG. 2a is a schematic view illustrating a system for determining the absolute value of ICP in accordance with a first embodiment of the present invention which relies upon measurement of displacement of skull bones.
Figure 2B:
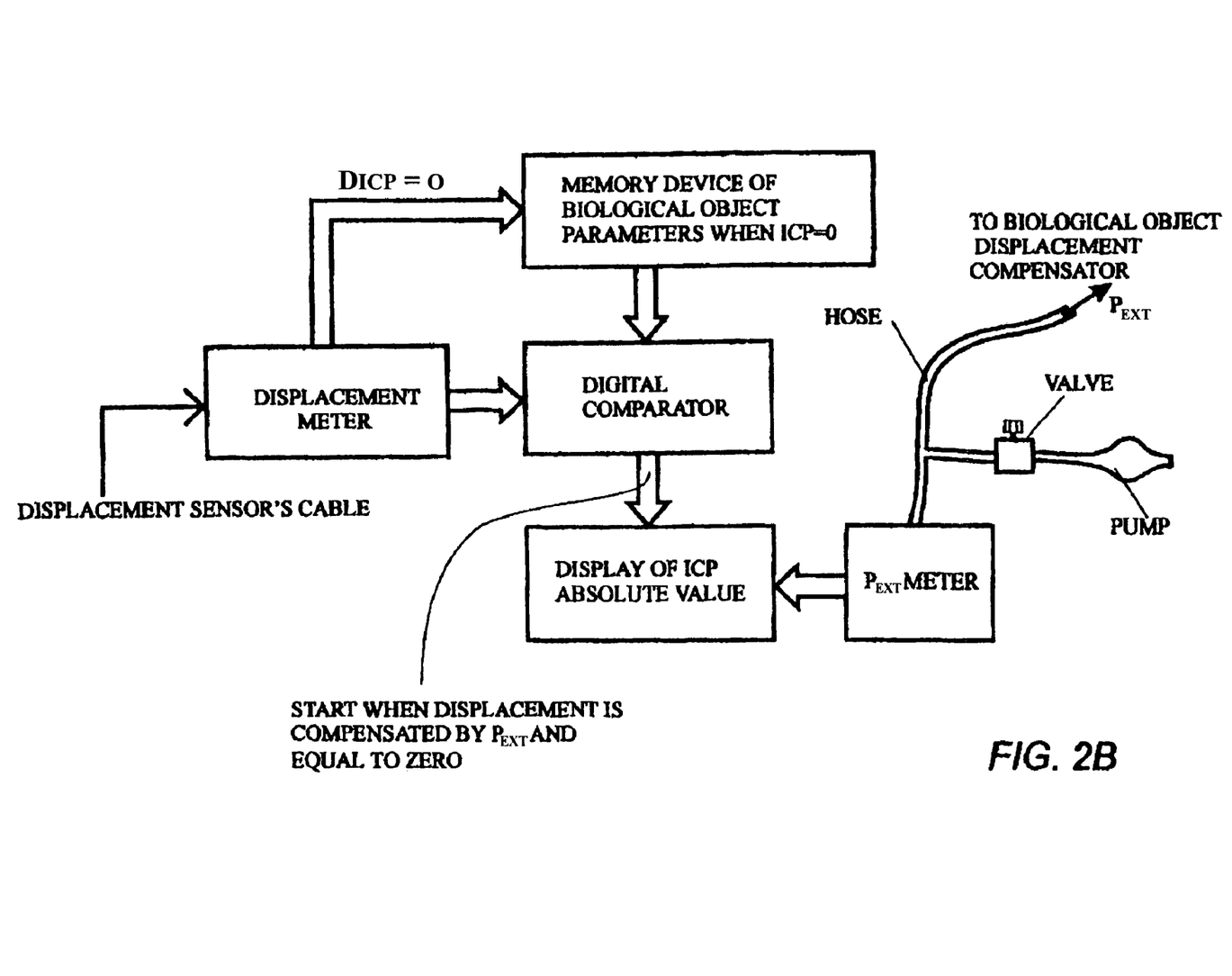
Figure 2C:
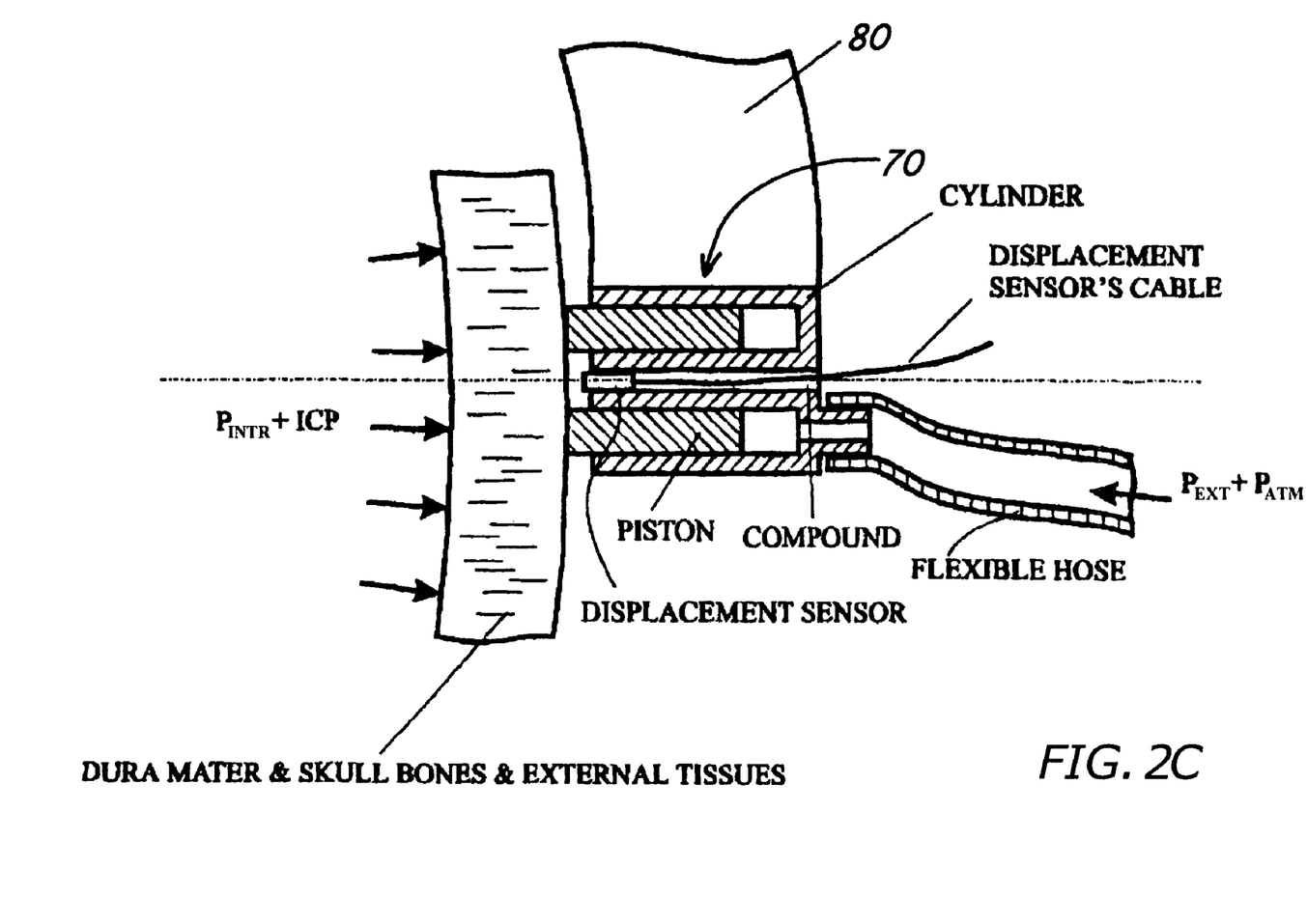
Figure 2D:
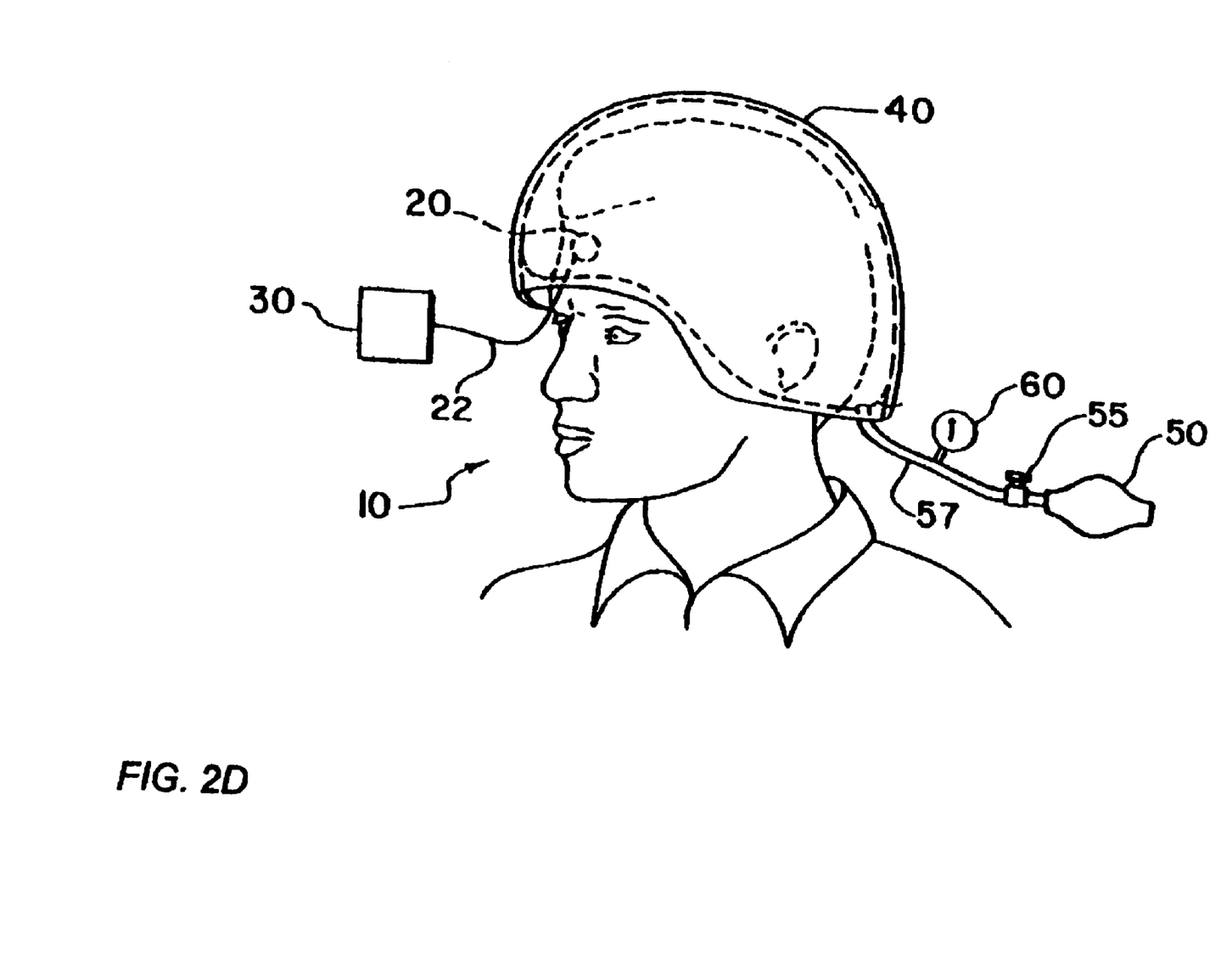
FIG. 2d is a schematic view illustrating a system for determining the absolute value of ICP in accordance with a second embodiment of the present invention which relies upon measurement of displacement of skull bones.

The external pressure $P_{EXT}$ can be induced by any of several systems 10, e.g., by a rigid helmet 40 containing an inflatable skull cap, in which a pressure $P_{EXT}$ is applied to the cranial vault by means of flexible hose 57, a pump 50, a valve 55 and a manometer or other pressure $P_{EXT}$ measuring device 60 (see FIG. 2D). In another embodiment, the external pressure for the local movement of displaced skull bones to the initial location can be induced by a cylinder and piston system 70 (see FIGS. 2A and 2C) that is fixed on the human head by a rigid mechanical frame 80 (see FIG. 2A). The displacement can be measured by many acceptable known sensors 20 such as ultrasonic distance sensors, capacitive sensors, electromagnetic, optic sensors, etc. connected to a processor 30 or the like via a cable 22.

Figure 3A:
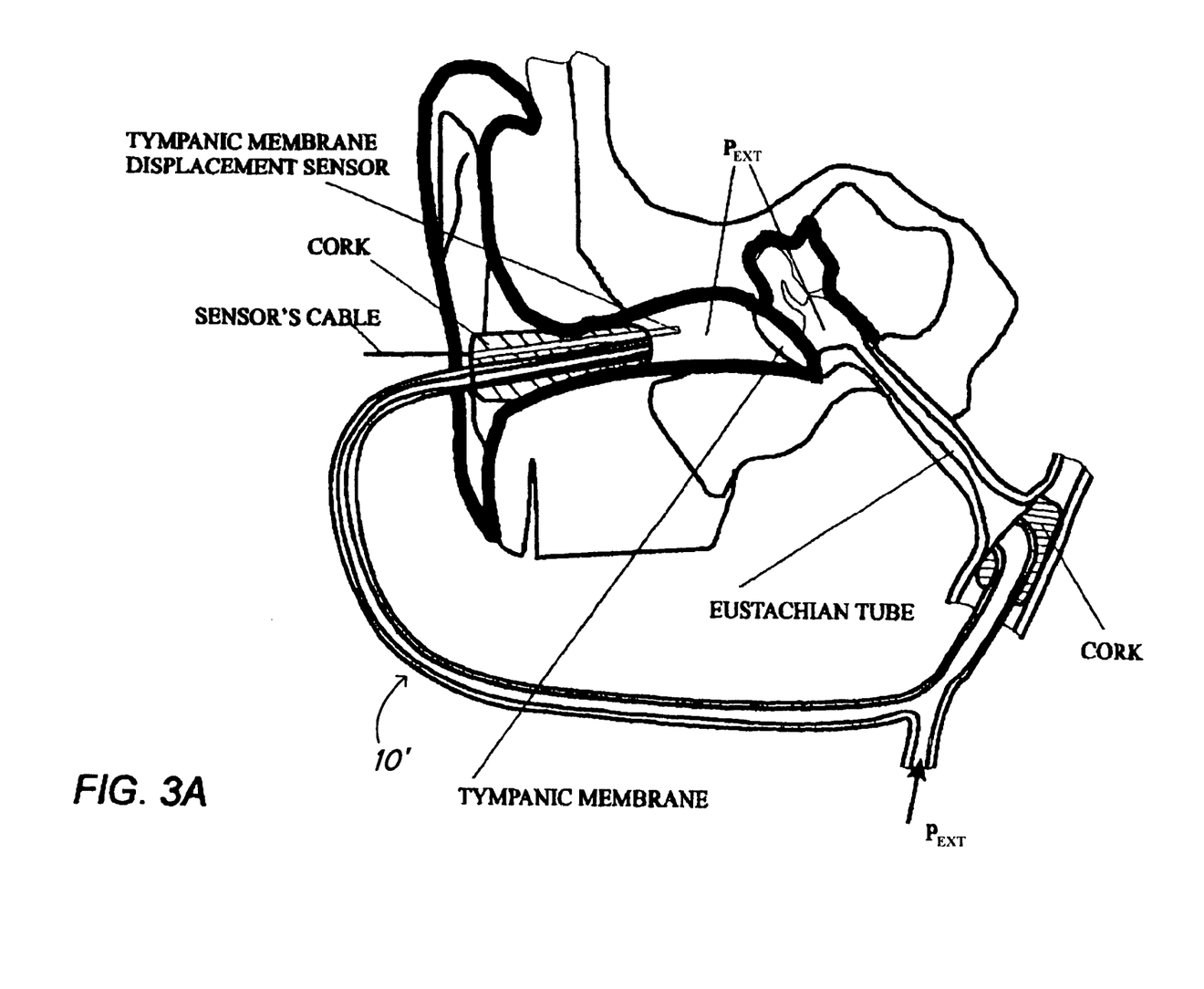
FIG. 3a is a schematic view illustrating a system for determining the absolute value of ICP in accordance with a third embodiment of the present invention which relies upon measurement of displacement of the tympanic membrane of the ear.
Figure 3B:
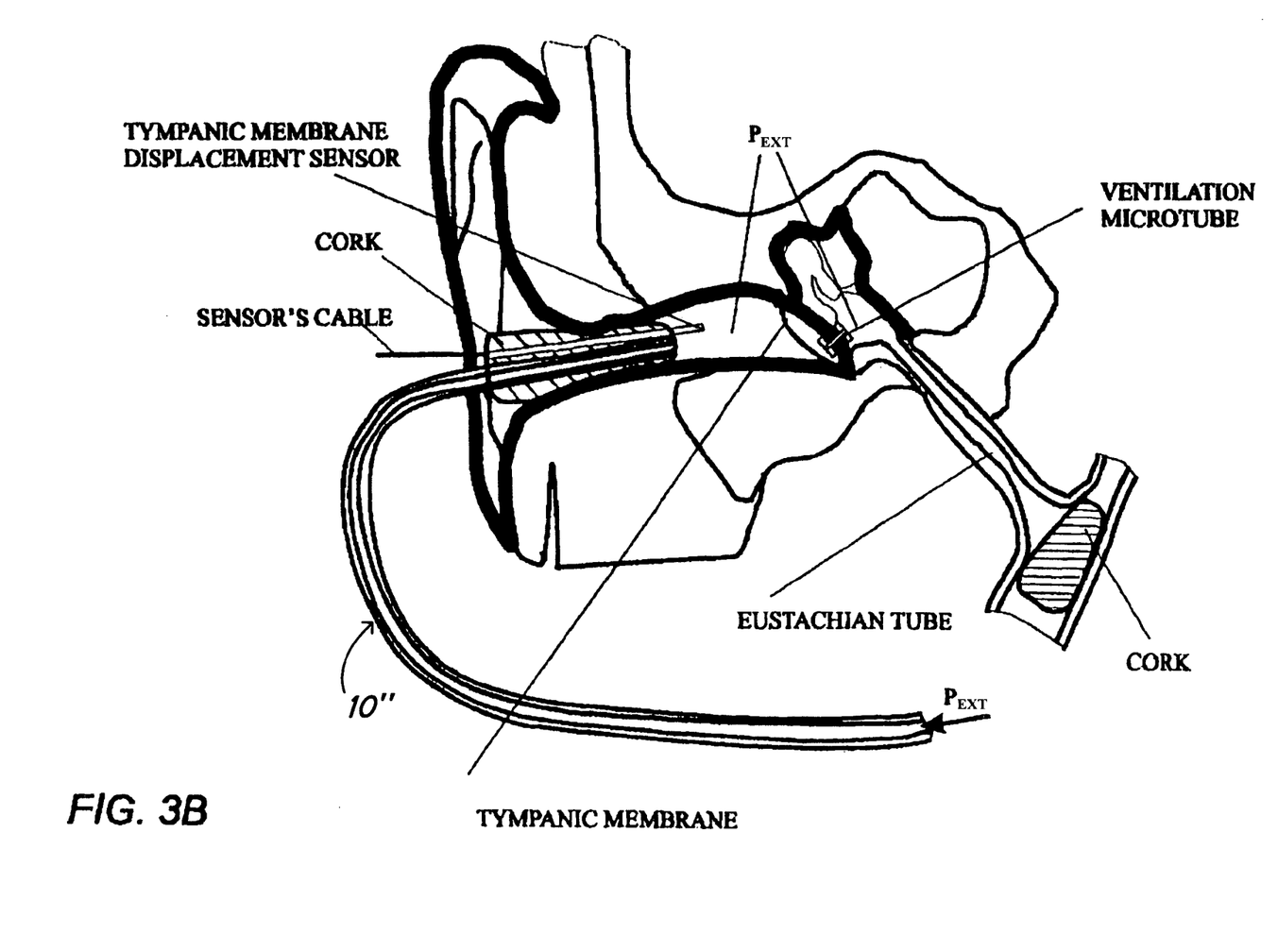
FIG. 3b is a schematic view illustrating a system for determining the absolute value of ICP in accordance with a fourth embodiment of the present invention which relies upon measurement of displacement of the tympanic membrane of the ear.

Referring now to FIGS. 3A and 3B, embodiments of system 10', 10" are shown in which displacement of the tympanic membrane rather than of the skull bones is measured. The external pressure for the displacement of the tympanic membrane to the initial position can also be induced by the means of flexible hose, a pump, a value and a manometer or other pressure $P_{EXT}$ measuring device (See FIGS. 3A and 3B). But in this case, it is necessary to apply simultaneously the same pressure $P_{EXT}$ to the inner ear and externally to the tympanic membrane (see FIGS. 3A and 3B). If it is impossible to apply the pressure $P_{EXT}$ to the inner ear through the Eustachian tube (as is done in FIG. 3A) a ventilation microtube needs to be used (as shown in FIG. 3B).

Methods of the invention include the identification of the biological object BO which could be displaced by the ICP>0 (such as the tympanic membrane, skull bones, etc.) and the subsequent displacement thereof by an external pressure.

The method includes the identification of individual characteristics or parameters of this biological object BO when ICP=0 and when the displacement is equal to zero (see FIG. 1A). Any known method of displacement measurement could be applied for accomplishing this measurement, namely a) the direct measurement of displacement (optical methods, laser interpherometry, imaging with digital TV cameras, MRI, CT, etc.); or b) indirect measurement of displacement (ultrasonic distance meters, semiconductor force sensors, ultrasonic surface acoustic waves and resonance spectrum meters, acoustic and impedance meters, etc.).

It is possible to achieve ICP=0 by a body tilting its head up (healthy person, mild and minor head injury, 86% of severe head injuries) or by measuring characteristics and parameters of the biological object BO during or just after neurosurgery when the brain is opened or just closed.

If ICP>0, the method of this invention can identify the change of measured characteristics or parameters of BO, caused by a displacement, which is greater than zero.

An external pressure $P_{EXT}$ is then applied to the cranium when ICP>0 until the characteristics or parameters of the biological object BO will again be equal to the initial characteristics or parameters, as measured when displacement is equal to zero, in order to obtain the condition when $P_{EXT}$=ICP. The value of $P_{EXT}$=ICP is stored or registered when the zero displacement status of BO is achieved.

The processor may include a digital memory device of the shape or its parameters of elastic biological object (skull bones, tympanic membrane, etc.), a digital comparator of initial shape (or its parameters) when ICP=0 and the shape when ICP>0. This digital comparator generates the "start" signal to display ICP absolute value in the case when the displacement is fully compensated by external applied pressure $P_{EXT}$.

This method is shown in greater detail in FIG. 2B. A condition where ICP=0 is created by a body tilting its head up (healthy person, mild and minor head injury, 86% of severe head injuries) or by measuring characteristics and parameters of the biological object BO during or just after neurosurgery when the brain is opened or just closed. The displacement sensor measures and transmits a value for displacement when ICP=0 ($D_{ICP=0}$) to a memory device, which stores this value. Later, when ICP>0, the displacement sensor is used to measure and transmit a value for displacement when ICP>0 ($D_{ICP>0}$) to a digital comparator on a continuous or periodic basis. External pressure $P_{EXT}$ is applied (for example on a slowly increasing basis). At the moment when the digital comparator determines that the biological object has returned to its original position (i.e., when $D_{ICP>0}=D_{ICP=0}$), ICP is determined to be the external pressure $P_{EXT}$ and is stored and/or displayed.

The present invention, therefore, provides a system and method for determining the absolute value of ICP which is non-invasive, which can be used without performing calibration thereof, which is relatively simple to use, and which is safe and dependable.

Although the invention has been described with reference to a particular arrangement of parts, features and the like, these are not intended to exhaust all possible arrangements or features, and indeed many other modifications and variations will be ascertainable to those of skill in the art.

What is claimed is:

1. A method for obtaining an indication of the intracranial pressure of a living body, comprising the steps of:
    determining an initial position of an elastic biological object when the intracranial pressure within the living body is zero;
    determining a subsequent position of the elastic biological object when the intracranial pressure within the living body is unknown but greater than zero;
    applying an external pressure to the elastic biological object; and
    identifying the unknown intracranial pressure of the living body as that external pressure which causes the subsequent position to be equal to the initial position.

2. The method of claim 1 wherein the elastic biological object comprises a skull bone.

3. The method of claim 2 wherein the applying an external pressure step comprises the step of inflating an inflatable helmet.

4. The method of claim 2 wherein the applying an external pressure step comprises the step of actuating a piston and cylinder assembly mounted on a frame.

5. The method of claim 1 wherein the elastic biological object comprises a tympanic membrane of an ear.

6. The method of claim 5 wherein the applying an external pressure step comprises the step of flowing fluid through a tube adapted for insertion into an ear.

7. A method for obtaining a measurement of the absolute pressure inside a cranium, comprising the steps of:
    determining a first position of a physiological object when the intracranial pressure is balanced with atmospheric pressure;
    exposing the physiological object to intracranial pressure causing said physiological object to move to a second position;
    applying a force against the physiological object until the position of the object is restored to its first position and storing a value of the force at which this occurs; and
    converting the stored value to a measurement of the absolute pressure inside a cranium.

8. The method of claim 7 wherein the physiological object comprises a skull bone.

9. The method of claim 8 wherein the applying a force step comprises the step of inflating an inflatable helmet.

10. The method of claim 8 wherein the applying a force step comprises the step of actuating a piston and cylinder assembly mounted on a frame.

11. The method of claim 7 wherein the physiological object comprises a tympanic membrane of an ear.

12. The device of claim 11 wherein the applying a force step comprises the step of flowing fluid through a tube adapted for insertion into an ear.

* * * * *

UNITED STATES PATENT AND TRADEMARK OFFICE
Certificate

Patent No. 7,147,605 B2                                                                 Patented: December 12, 2006

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Arminas Ragauskas, Kaunas (LT); and Gediminas Daubaris, Kaunas (LT).

Signed and Sealed this Twenty-second Day of April 2014.

JEFFREY G. HOEKSTRA
*Supervisory Patent Examiner*
Art Unit 3736
Technology Center 3700